United States Patent [19]

Goetinck et al.

[11] Patent Number: 5,686,059
[45] Date of Patent: Nov. 11, 1997

[54] CARTILAGE MATRIX PROTEIN AND METHODS FOR USE

[75] Inventors: Paul F. Goetinck, Boston; Mehrdad Tondravi, Marshfield, both of Mass.

[73] Assignee: The General Hospital Corporation, Boston, Mass.

[21] Appl. No.: 462,128

[22] Filed: Jun. 5, 1995

Related U.S. Application Data

[63] Continuation of Ser. No. 6,096, Jan. 15, 1993, abandoned, which is a continuation-in-part of Ser. No. 866,403, Apr. 10, 1992, abandoned.

[51] Int. Cl.$^6$ .......................... A61K 49/00; A61K 38/06; A61K 38/17; C07K 1/00
[52] U.S. Cl. .......................... 424/9.1; 424/1.11; 530/357; 530/350
[58] Field of Search .......................... 435/172.3; 514/12; 530/300, 324, 328, 350; 424/1.11, 9.1

[56] References Cited

U.S. PATENT DOCUMENTS 5,043,429  8/1991  Zimmerman et al. .................. 530/383

FOREIGN PATENT DOCUMENTS

PCT/US93/03107  6/1993  WIPO.

OTHER PUBLICATIONS

Argraves et al., Proc. Nat'l. Acad. Sci. USA 84:464, 1987.
Bonaldo et al., Biochemistry 29:1245, 1990.
Gerecke, "Two Alternative Forms of Type XII Collagen Molecules are Multidomain Structures Containing von Willebrand Factor A and Fibronectin Type III Repeats", Harvard University, Cambridge, Massachusetts, 1992.
Jenkins et al., J. Biol. Chem. 265:19624, 1990.
Kiss et al., J. Biol. Chem. 264:8126, 1989.
Kiss et al., Molecular and Cellular Biology, vol. 10, No. 5, Issued May, 1990, pp. 2432–2436.
Pareti et al., J. Biol. Chem. 28:13835, 1987.
Goetinck et al., Annals of the New York Academy of Sciences 559:29, 1990.
Stirpe et al., Development 107:23, 1989.
Tsonis et al., Exp. Eye Res. 46:753–764, 1988.
Tsonis et al., Biochem. Journal 254:623, 1988.
Louis et al. "Autoprocessing of the HIV–1 protease using . . . " Eur. J. Biochem. 199, 361–369. 1991.

*Primary Examiner*—Robert A. Wax
*Assistant Examiner*—Nashaat T. Nashed
*Attorney, Agent, or Firm*—Louis Myers; Lahive & Cockfield

[57] ABSTRACT

DNA constructs coding for a chimeric polypeptides containing fragments of cartilage matrix proteins that can bind collagen and their protein products are described. Also, the invention relates to purified chimeric polypeptides, and methods of their production and purification from transformed cells as well as their use as agents in therapeutics and clinical imaging. In addition, the invention disclosed a method for forming collagen fibrils using the chimeric polypeptide.

4 Claims, 2 Drawing Sheets

| | |
|---|---:|
| MRVLSGTSLMLCSLLLLQALCSPGLAPQSRGHLCRTRPTDLVFVVDSSR | 50 |
| SVRPVEFEKVKVFLSQVIESLDVGPNATRVGMVNYASTVKQEFSLRAHVS | 100 |
| KAALLQAVRRIQPLSTGTMTGLAIQFAITKAFGDAEGGRSRSPDISKVVI | 150 |
| VVTDGRPQDSVQDVSARARASGVELFAIGVGSVDKATLRQIASEPQDEHV | 200 |
| DYVESYSVIEKLSRKFQEAFCVVSDLCATGDHDCEQVCISSPGSYTCACH | 250 |
| EGFTLNSDGKTCNVCSGGGGSSATDLVFLIDGSKSVRPENFELVKKFISQ | 300 |
| IVDTLDVSDKLAQVGLVQYSSSVRQEFPLGRFHTKKDIKAAVRNMSYMEK | 350 |
| GTMTGAALKYLIDNSFTVSSGARPGAQKVGIVFTDGRSQDYINDAAKKAK | 400 |
| DLGFKMFAVGVGNAVEDELREIASEPVAEHYFYTADFKTINQIGKKLQKK | 450 |
| ICVEEDPCACESLVKFQAKVEGLLQALTRKLEAVSKRLAILENTVV | 496 |

SEQ ID NO:37

*FIG. 3*

CARTILAGE MATRIX PROTEIN AND METHODS FOR USE

This application is a continuation of application Ser. No. 08/006,096 filed on Jan. 15, 1993, now abandoned which is a continuation in part of application Ser. No. 07/866,403 filed Apr. 10, 1992, now abandoned Entitled: CARTILAGE MATRIX PROTEIN AND METHODS FOR USE.

BACKGROUND OF THE INVENTION

This invention was made with Government support under Contract #ND 22016 and DK 28433 awarded by the National Institutes of Health. The Government has certain rights in this invention.

This invention relates to cartilage matrix protein.

Cartilage matrix protein (CMP) is a noncollagenous protein of the extracellular matrix of cartilage. CMP is a homotrimer of disulfide bond linked subunits.

Argraves et al. (*Proc. Nat'l. Acad. Sci.* USA 84:464, 1987) and Kiss et al. (*J. Biol. Chem.* 264:8126, 1989) disclose that chicken CMP includes a domain (residues 148–183) with significant homology to epidermal growth factor and two homologous repeat sequences (residues 30–220 and 262–450). The homologous repeats (CMP-1 and CMP-2 respectively) are homologous to regions within von Willebrand factor, complement factor B, complement factor C2, type VI collagen, and the α chains of the integrins Mac-1, p150,95 and LFA-1 (see Kiss et al., supra for a review).

Human CMP is 79% identical to chicken CMP overall; human and chicken CMP-1 domains are 79% identical; human and chicken CMP-2 domains are 84% identical (Jenkins et al., *J. Biol. Chem.* 265:19624, 1990).

CMP may interact with both proteoglycan and collagen (Goetinck et al., *Annals of the New York Academy of Sciences* 599:29, 1990).

Bonaldo et al. (*Biochemistry* 29:1245, 1990) report that type VI collagen has several repeats homologous to CMP and that a region which includes these repeats is involved in interactions between type VI collagen and type I collagen.

SUMMARY OF THE INVENTION

In general, the invention features a polypeptide (preferably substantially pure) which is a fragment or analog of cartilage matrix protein, the polypeptide being capable of binding collagen.

In various preferred embodiments: the polypeptide includes CMP-1 or CMP-2; the polypeptide includes a fragment or analog of CMP-1 or CMP-2; the polypeptide is or comprises all or part of CMP-1, e.g., an N-terminal fragment of CMP-1 approximately 45 amino acids in length, or the approximately 8–10 residue collagen binding sequence 1 (CBS1, defined in detail below) motif; the polypeptide is or comprises all or part of CMP-2, e.g., a N-terminal fragment of CMP-2 approximately 45 amino acids in length, or the approximately 8–10 residue CBS1 motif of CMP-2; the polypeptide is or comprises a CBS1 motif; and the polypeptide is all or part of CMP-1 and CMP-2.

In a related aspect, the invention features a method for forming collagen fibrils. The method includes contacting cartilage matrix protein, or a polypeptide of the invention, with collagen.

In preferred embodiments the polypeptide is fragment or analog of cartilage matrix protein; is a fragment or analog of cartilage matrix protein domain CMP-1 or CMP-2; includes or consists essentially of a CBS1 motif; includes or consists essentially of an N-terminal fragment of CMP-1 approximately 45 amino acids residues in length; consists essentially of or includes the CBS1 motif of CMP-1; includes or consists essentially of an N-terminal fragment of CMP-2 approximately 45 amino acid residues in length; consists essentially of or includes the CBS1 motif of CMP-2.

In another related aspect, the invention features a method for delivering a compound to a tissue, e.g., a collagenous tissue, the method includes administering to a patient the compound linked to a polypeptide of the invention.

In preferred embodiments the polypeptide is fragment or analog of cartilage matrix protein; is a fragment or analog of cartilage matrix protein domain CMP-1 or CMP-2; includes or consists essentially of a CBS1 motif; includes or consists essentially of an N-terminal fragment of CMP-1 approximately 45 amino acids residues in length; consists essentially of or includes the CBS1 motif of CMP-1; includes or consists essentially of an N-terminal fragment of CMP-2 approximately 45 amino acid residues in length; consists essentially of or includes the CBS1 motif of CMP-2.

In another aspect, the invention features a molecular conjugate which includes a polypeptide which is collagen-binding fragment of cartilage matrix protein and an imaging or therapeutic agent.

In preferred embodiments the polypeptide is fragment or analog of cartilage matrix protein; is a fragment or analog of cartilage matrix protein domain CMP-1 or CMP-2; includes or consists essentially of a CBS1 motif; includes or consists essentially of an N-terminal fragment of CMP-1 approximately 45 amino acids residues in length; consists essentially of or includes the CBS1 motif of CMP-1; includes or consists essentially of an N-terminal fragment of CMP-2 approximately 45 amino acid residues in length; consists essentially of or includes the CBS1 motif of CMP-2.

In another aspect the invention features a method of promoting the attachment of collagen to a surface including coating the surface with a collagen binding fragment of collagen matrix protein and contacting said coated surface with collagen.

In preferred embodiments the polypeptide is fragment or analog of cartilage matrix protein; is a fragment or analog of cartilage matrix protein domain CMP-1 or CMP-2; includes or consists essentially of a CBS1 motif; includes or consists essentially of an N-terminal fragment of CMP-1 approximately 45 amino acids residues in length; consists essentially of or includes the CBS1 motif of CMP-1; includes or consists essentially of an N-terminal fragment of CMP-2 approximately 45 amino acid residues in length; consists essentially of or includes the CBS1 motif of CMP-2.

In preferred embodiments the surface is a surface of a device to be implanted in the body of a recipient.

In another aspect the invention features a substantially purified DNA encoding a polypeptide of the invention; a vector including a DNA sequence of the invention; a cell containing DNA encoding a polypeptide of the inventions e.g., cell capable of expressing the polypeptide; an essentially homogeneous population of cells, each of which comprises the DNA encoding a polypeptide of the invention; and a polypeptide produced by expression of DNA encoding a polypeptide of the invention.

In another aspect the invention includes a therapeutic composition including a polypeptide of the invention and a pharmaceutically acceptable carrier.

In another aspect the invention features a method for manufacture of a polypeptide of the invention including culturing a cell containing DNA encoding a polypeptide of the invention in medium to express the polypeptide.

The nucleotide sequence of chicken CMP is available from GenBank™/EMBL Data Bank under accession numbers X12346–X12354. The nucleotide sequence of human CMP is available from GenBank™/EMBL Data Bank under accession numbers Jo5666 and JO5667.

CMP-1 (the CMP-1 domain) is a sequence corresponding to amino acids 30–220 of chicken CMP; CMP-2 (the CMP-2 domain) is a sequence corresponding to amino acids 262–450 of CMP (numbering according to Kiss et al., supra). CMP-1 also corresponds to amino acids 23 to 222 of human CMP, and CMP-2 also corresponds to amino acids 264–453 of human CMP (numbering according to Jenkins et al., supra). The term CMP-1 also includes polypeptides corresponding to domains in proteins such as the von Willebrand factor, complement factor B, complement factor C2, type VI collagen, and the α chains of the integrins Mac-1, p150,95 and LFA-1 that are homologous the to human or chicken CMP-1 domain. The term CMP-2 also includes polypeptides corresponding to domains in proteins such as the von Willebrand factor, complement factor B, complement factor C2, type VI collagen, and the α chains of the integrins Mac-1, p150,95 and LFA-1 that are homologous to the human or chicken CMP-2 domain. Such homologous domains have been identified by standard techniques (see Kiss et al., supra for a review). Such domains are 70% homologous, preferably 80%, more preferably 90% homologous to the human CMP-1 domain or the human CMP-2 domain.

The CBS1 motif is an 8–10 amino acid sequence found in CMP-1, CMP-2, and a large number of other proteins, some or many of which bind collagen. The CBS1 motif is located at amino acids 38–47 (in CMP-1) (TDLVFIIDSS) (SEQ. ID NO: 1) and 271–280 (in CMP-2) (LDLVFLIDGS) (SEQ. ID. NO. 2) of chicken CMP (numbering according to Kiss et al., supra). The CBS1 motif corresponds to amino acids 40–49 (in CMP-1) (TDLVFVVDSS) (SEQ. ID. NO: 3) and 274–283 (in CMP-2) (TDLVFLIDGS) (SEQ. ID. NO: 4) of human CMP (numbering according to Jenkins et al., supra). The CBS1 motif also includes the homologous 8–10 amino acid residue sequence found in CMP-1-like and CMP-2-like domains of other proteins, particularly collagen binding proteins such as the von Willebrand factor, complement factor B, complement factor C2, type VI collagen, and the α chains of the integrins Mac-1, p150,95 and LFA-1. Such homologous domains have been identified by standard techniques (see Kiss et al., supra for a review). Such domains are preferably 60–70% homologous, more preferably 80%, most preferably 90% homologous to the human CBS1 of the CMP-1 or CMP-2 domain. The invention includes the CBS1 domains from the following proteins (the protein is given first then residues 2–10 of the CBS1 domain is listed): α1 (XII) vW1, DIVFLTDAS (SEQ ID NO: 5); α1 (XII) vW2, DIVLLVDGS (SEQ ID NO: 6); α1; α1 (XII) VA, DLVFLVDGS (SEQ ID NO: 7); α1 (XII) VB, DWFLVDGS (SEQ ID NO: 8); α1 (XIV) vW1, DLVFLVDGS (SEQ ID NO: 9); CMP1; CMP1, DLVFIIDSS (SEQ ID NO: 10); CMP2, DLVFLIDGS (SEQ ID NO: 11); α1 (VI) A'1, DIMLLVDSS (SEQ ID NO: 12); α1 (VI) A'2, DLLFVLDSS (SEQ ID NO: 13); α1 (VI) A'3, DLFFVLDTS (SEQ ID NO: 14); α2 (VI) D3, DIVFLLDGS (SEQ ID NO: 15); α2 (VI) D2, DIMFVIDSS (SEQ ID NO: 16); α3 (VI) A'1, DIAFIMDSS (SEQ ID NO: 17); α3 (VI) A'2, ELAFAIDTS (SEQ ID NO: 18); α3 (VI) A'3, DVILGFDVS (SEQ ID NO: 19); α3 (VI) A1, DIVFLLDGS (SEQ ID NO: 20); α23; α3 (VI) A2, DWFLIDSS (SEQ ID NO: 21); α3 (VI) A3, DWFLVDGS (SEQ ID NO: 22); α3 (VI) A4, DWFLIDGS (SEQ ID NO: 23); α3 (VI) A5, DILFLIDGS (SEQ ID NO: 24); α3 (VI) A6, DIIFLLDGS (SEQ ID NO: 25); α3 (VI) A7, DIVFLIDGS (SEQ ID NO: 26); α3 (VI) A8, DLIFLIDGS (SEQ ID NO: 27); HUM vWF A1, DLVFLLDGS (SEQ ID NO: 28); HUM vWF A2, DVAFVLEGS (SEQ ID NO: 29); HUM vWF A3, DVILLLDGS (SEQ ID NO: 30); HUM Mac-1, DIVFLIDGS (SEQ ID NO: 31); HUM p150,95, DIVFLIDGS (SEQ ID NO: 32); HUM LFA1, DLVFLFDGS (SEQ ID NO: 33); RAT VLA-1, DIVIVLDGS (SEQ ID NO: 34); HUM VLA-2, DWLVCDES (SEQ ID NO: 35); HUM VLA-4, DISFLLDVS (SEQ ID NO: 36).

Fragments or analogs of CMP capable of binding collagen can be identified using the assay described below.

Fragments or analogs of CMP useful for forming collagen fibrils include those which have an effect on fibril formation as assayed by the fibrillogenesis assay described below. Any fragment or analog which substantially affects fibrillogenesis will cause a change in the optical density profile in this assay. Microscopic examination (described below) of the resulting fibrils can then be used to determine the exact effect of the CMP fragment or analog on fibril morphology.

The invention includes CMP and CMP polypeptides which are substantially homologous to human CMP as well as other naturally occurring mammalian and avian CMP. Also included are: allelic variations; natural mutants; and induced mutants; Also included are CMP and CMP polypeptides encoded by DNA that hybridizes under high or low (e.g., washing at 2×SSC at 40° C. with a probe length of at least 40 nucleotides) stringency conditions to a nucleic acid naturally occurring (for other definitions of high and low stringency see *Current Protocols in Molecular Biology*, John Wiley & Sons, New York, 1989, 6.3.1 –6.3.6, hereby incorporated by reference).

The invention also includes analogs of naturally occurring CMP polypeptides. Analogs can differ from naturally occurring CMP by amino acid sequence differences or by modifications that do not affect sequence, or by both. Analogs of the invention will generally exhibit at least 70%, more preferably 80%, more preferably 90%, and most preferably 95% or even 99%, homology with all or part of a naturally occurring CMP sequence (intact CMP, CMP-1 or CMP-2). The length of comparison sequences will generally be at least about 6–8 amino acid residues, usually at least 20 amino acid residues, more usually at least 24 amino acid residues, typically at least 28 amino acid residues, and preferably more than 35 amino acid residues. Modifications include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps, e.g., by exposing the polypeptide to enzymes that affect glycosylation derived from cells that normally provide such processing, e.g., mammalian glycosylation enzymes. Also embraced are versions of the same primary amino acid sequence that have phosphorylated amino acid residues, e.g., phosphotyrosine, phosphoserine, or phosphothreonine. Analogs can differ from naturally occurring CMP by alterations of their primary sequence. These include genetic variants, both natural and induced. Induced mutants may be derived by various techniques, including random mutagenesis of the encoding nucleic acids using irradiation or exposure to ethanemethylsulfate (EMS), or may incorporate changes produced by site-specific mutagenesis or other techniques of molecular biology. Also included are analogs that include residues other than naturally occurring L-amino acids, e.g., D-amino acids or non-naturally occurring or synthetic amino acids, e.g., β or γ amino acids. Peptides with N-terminal or C-terminal modifications to enhance peptide stability are also within the invention. Cyclic forms of the polypeptides of the invention are within the invention.

In addition to substantially full-length polypeptides, the invention also includes biologically active e.g., collagen binding, fragments of the polypeptides. As used herein, the term "fragment", as applied to a polypeptide, will ordinarily be at least about 6–10 contiguous amino acids, typically at least about 20 contiguous amino acids, more typically at least about 30 contiguous amino acids, usually at least about 40 contiguous amino acids, preferably at least about 50 contiguous amino acids, and most preferably at least about 60 to 80 or more contiguous amino acids in length. Fragments of CMP can be generated by methods known to those skilled in the art. The ability of a candidate fragment to exhibit a biological activity of CMP can be assessed by methods known to those skilled in the art. Also included are CMP polypeptides containing amino acids that are normally removed during protein processing, including additional amino acids that are not required for the biological activity of the polypeptide, or including additional amino acids that result from alternative mRNA splicing or alternative protein processing events.

The invention also includes DNA, preferably substantially pure DNA, encoding the polypeptides of the invention. The invention also includes antibodies, e.g., monoclonal antibodies, directed against the polypeptides of the invention. The invention also includes a chimeric polypeptide which includes a polypeptide of the invention.

A CMP polypeptide, fragment, or analog is biologically active if it exhibits a biological activity of a naturally occurring CMP, e.g., binding collagen or affecting fibrillogenesis.

Substantially pure DNA is DNA that is not immediately contiguous with both of the coding sequences with which it is immediately contiguous (i.e., one at the 5' end and one at the 3' end) in the naturally-occurring genome of the organism from which the DNA of the invention is derived.

Homologous refers to the sequence similarity between two polypeptide molecules or between two nucleic acid molecules. When a position in both of the two compared sequences is occupied by the same base or amino acid monomeric subunit, e.g., if a position in each of two DNA molecules is occupied by adenine, then the molecules are homologous at that position. The homology between two sequences is a function of the number of matching or homologous positions shared by the two sequences. For example, 6 of 10, of the positions in two sequences are matched or homologous then the two sequences are 60% homologous. By way of example, the DNA sequences ATTGCC and TATGGC share 50% homology.

A substantially pure preparation of a polypeptide is a preparation which is substantially free of the proteins with which it naturally occurs in a cell.

Other features and advantages of the invention will be apparent from the following description of the preferred embodiments thereof, and from the claims.

DETAILED DESCRIPTION

Brief Description of the Drawings The drawings are first briefly described.

FIG. 3 depicts the amino acid sequence of human CMP. (SEQ ID NO: 37)

Cartilage Matrix Protein

Figure 1:
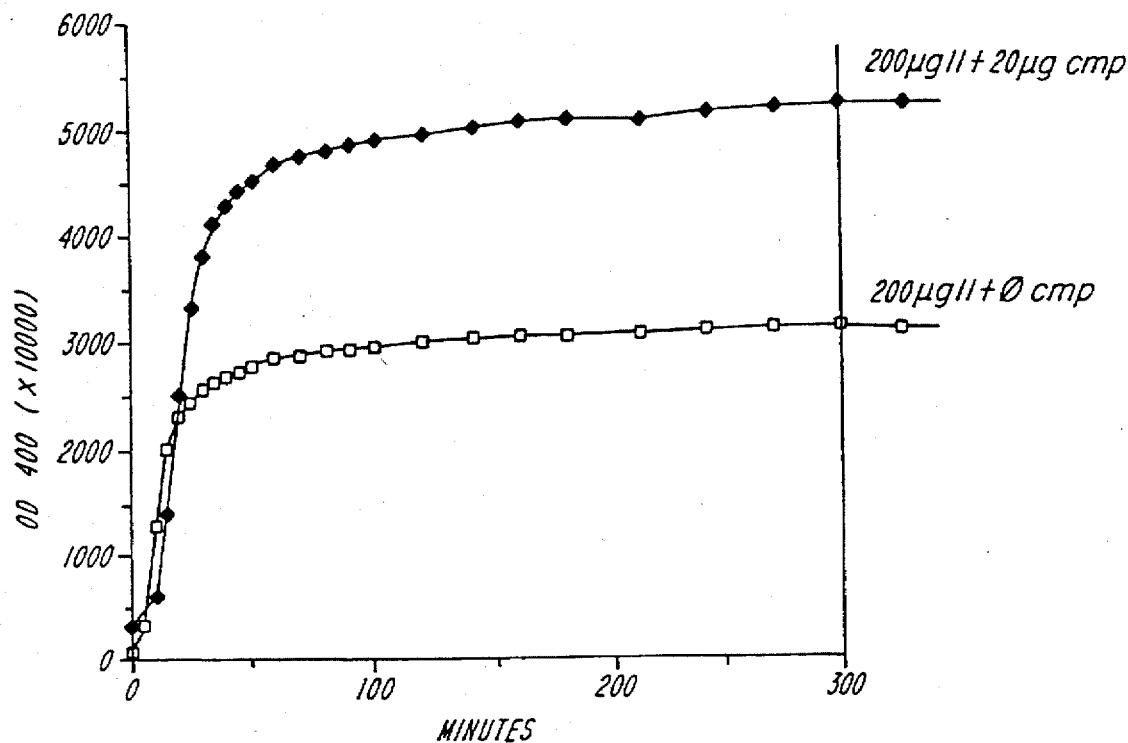
FIG. 1 is a graph which depicts the results of a fibrillogenesis assay. Optical density (x1000) at 400 nm is plotted as a function of time (min) for reactions carried out in the presence (open squares) and absence (filled diamonds) of cartilage matrix protein).

Described below are methods for producing CMP in bacterial cells, generating CMP fragments, determining whether a given CMP fragment binds to collagen, determining whether a given CMP fragment influences fibrillogenesis, as well as methods for using CMP and fragments thereof.

Binding Studies Demonstrate the Interaction of CMP and Type II Collagen

An ELISA, performed as described below, demonstrated that CMP interacts with type II collagen. This assay was also used to demonstrate the binding of reduced and alkylated cartilage matrix protein to type II collagen. CMP and reduced and alkylated CMP bound in a concentration-dependent manner, as detected by an anti-cartilage matrix mAb (III-D5). The interaction between CMP and collagen could also be demonstrated when CMP was immobilized and the binding of soluble type II collagen was detected with a mAb which recognizes type II collagen (I-B4). The binding of collagen to immobilized CMP was inhibited by soluble CMP, demonstrating that the interaction is specific. Reduced and alkylated CMP was equally effective in this inhibition. Bovine serum albumin did not inhibit binding in this assay, whereas relatively high concentrations of link protein showed a minor inhibition which could be due to residual traces of CMP in the link protein preparation. However, link protein has previously been shown to bind to types I and II collagen (Chandrasekhar et al., *J. Biol. Chem.* 258:6226, 1983) and, at high levels, this binding may interfere with the binding of CMP to collagen.

Bacterial CMP Expression

The isolation of partial cDNA clones of CMP has been previously described, and the entire CMP coding sequence was determined from these cDNA clones and from sequencing of the exonic fragments of a genomic clone (Argraves et al., supra; Kiss et al., supra). The longest cDNA clone pCMP4 (1.304 nucleotides long) spanned an EcoRI site 53 nucleotides 3' to the translation termination codon and extended in the 5' direction to contain 1,251 out of 1,482 nucleotides of the coding sequence. A full-length CMP cDNA was constructed by using an oligonucleotide primer overlapping a unique Sst I site near the 5' end of pCMP4 clone to synthesize a first strand cDNA extending from the Sst I site to the 5' end of the mRNA. A second oligonucleotide which overlaps the AUG initiation codon of CMP and generates a restriction site to facilitate cloning of the CMP cDNA in the same reading frame as the α-galactosidase gene of pUC119 was then used to amplify this fragment by the polymerase chain reaction (PCR). This PCR product was cloned as a KpnI-SstI fragment into the same sites of pUC119 and sequenced to insure that no mutations were inadvertently introduced during the reverse transcriptase or the PCR reactions. This clone is referred to as pCM5P'. Subsequently, the SstI-EcoRI fragment of pCMP4 was gel purified and cloned in the SstI-EcoRI site of pCMP5' to generate the full length CMP cDNA clone, pCMP-F1. For expression of full length mature CMP protein, the fragment of pCMP-F1 from the mature end of the protein (Alanine 24)

to the end of the CMP cDNA insert was amplified by PCR. The 5' PCR oligomer included an ATG initiation codon incorporated as part of an NcoI site; the 3' PCR oligomer also introduced an NcoI site at the 3' end of the PCR fragment. This fragment was purified, cut with NcoI and cloned into the NcoI site of the *E. coli* expression vector pET-11d (Novagen). The clone pET-CMP 1 containing the insert in the correct orientation was selected and sequenced to insure that inadvertent mutations were not introduced during the cloning procedure. The *E. coli* strain BL21(D3) pLysS (Novagen) was transformed with pET-CMP 1 and at appropriate times CMP expression was induced by isopropyl-β-D-thiogalactopyranoside.

Antibodies

Polyclonal antisera were generated in rabbits against CMP and a synthetic peptide corresponding to residues Phe$^{380}$-Val$^{424}$ of CMP (the numbers identifying the amino acids refer to the residue numbers in the primary translation product) conjugated to keyhole limpet hemocyanin, as described by Goetinck et al. (*J. Cell Biol.* 105:2403, 1987). Monoclonal antibodies were raised against a crude guanidine hydrochloride extract of sternal cartilage from 4–6 week-old chickens. ELISA screening showed that mAb III-D5 recognized CMP and I-B4 recognized type II collagen.

For use in electron microscopy, III-D5 ascites fluid and rabbit anti-Phe$^{380}$ -Val$^{424}$ serum were purified by affinity chromatography on a column of CMP-Sepharose. Polyclonal antisera to chicken cartilage type II collagen and aggrecan used in immunofluorescence studies were as described previously (Vertel et al., *Natl. Acad. Sci* USA 76:1261, 1979; Upholt et al., *Proc. Nat'l. Acad. Sci,* USA 76:4847, 1979).

Binding Assays

The interaction of CMP with collagen was studied using ELISA. Immobilization of CMP to microtitration plates (EIA, Linbro; Flow Laboratories, McLean, Va.) was carried out in 0.05M sodium carbonate buffer, pH 9.6 (60 µl/well), overnight at room temperature. Collagens (Type I, Collaborative Research Inc., Bedford, Mass.; Type II Nitta Gelatin Inc., Osaka, Japan; Types III, IV, and V, Calbiochem Corp., La Jolla, Calif.; type VI, Telios Pharmaceuticals, San Diego, Calif.; C1q, Center for Blood Research, Boston, Mass.) were immobilized in the same buffer by allowing the coating solution to dry at 37° C., overnight. All subsequent additions were for 1 hr in phosphate buffers saline, containing 0.05% Tween-20 (PBS-T). After each addition, plates were washed with PBS-T. The binding of collagen to plastic or to immobilized CMP was detected with mAb I-B4. The binding of CMP to plastic or to immobilized collagen was detected with mAb III-D5. The detecting monoclonals were followed in each case by peroxidase-conjugated rabbit anti-mouse IgG (H+L) and then peroxidase-substrate (BioRad Laboratories). Absorbance at 405 nm was determined and recorded using a microtitration-plate reader (Titertek Multiskan Plus, Flow Labs Inc., McLean, Va.).

Inhibition of collagen-CMP binding was undertaken by mixing various concentrations of inhibitor with collagen and allowing the mixture to stand for one hour prior to adding to CMP coated plates. Bound collagen was detected as described above.

Rotary Shadowing Studies Reveal the Molecular Interaction of CMP and type II Collagen In order to characterize the molecular sites of interaction of CMP and collagen, electron microscopic studies, using rotary shadowing of the components (performed as described below), were initiated. Isolated CMP molecules appeared as globular proteins comprised of two or three spherical domains connected by bent rods. Variations that were sometimes observed may be due to different angles of view. Isolated type II collagen molecules showed a typical rod-like structure of 280 nm in length. In mixtures of CMP and type II collagen, CMP was localized at both ends of the collagen molecule, resulting in the formation of concatenates. In addition to simple concatenation, networks of collagen molecules were also observed, with CMP-globules at the branch points.

Rotary Shadowing

Preparations of purified CMP or collagen were dialyzed against 0.1M ammonium acetate (HPLC grade, Sigma) pH 7.4, mixed with glycerol (40%) to a concentration of 25–50 µg/ml and nebulized onto freshly cleaved mica substrates (Engvall et al., *J. Cell. Biol.* 102:703, 1986). Each substrate was attached to a rotary stage in an Edwards E 306 vacuum evaporator (pumped to $10^{-6}$ Torr) at an angle of 5–10° to the twin electron beam source approximately 10 cm from the sample. Replicas were generated by evaporation of pure tungsten deposited to a thickness of 19–30 Å, as measured by a water cooled (quartz crystal) film thickness monitor (FTM4) (Peters, *B. Electronenmikroskop. Direktabh. Oberfl.* 12:377, 1979). The resulting films were backed by carbon evaporation, floated on a clean water surface, and picked up on 300 mesh grids for electron microscopy. Samples were viewed and photographed in an Hitachi H-600 STEM.

Nanomelia embryos were obtained from fertile eggs resulting from matings between parents heterozygous for the nanomalic mutation. These eggs were obtained from the Department of Animal Genetics, the University of Connecticut, through the courtesy of Dr. Louis J. Perro.

Immunolocalization Studies Demonstrate the Co-Localization of CMP and Type II Collagen in the Cartilage Extracellular Matrix The co-localization of CMP with type II collagen and aggrecan was examined in 5-day-old cultures of chicken sternal chondrocytes using double immunofluorescent staining reactions as described below. Chondrocytes were grown in the presence of ascorbic acid to facilitate the deposition of extracellular type II collagen fibrils. The extracellular localization of the monoclonal antibody III-D5 against CMP was compared with that of a polyclonal antiserum to type II collagen. A dense filamentous extracellular matrix pattern was observed for both CMP and type II collagen. In a separate experiment the extracellular localization of CMP was contrasted with that of aggrecan. The filamentous distribution of extracellular CMP did not co-localize with the amorphous pattern of aggrecan. Immunofluorescent staining of chondrocyte cultures carrying the genetic defect nanomelia, which is characterized by the absence of aggrecan in the cartilage extracellular matrix, demonstrated a similar co-localization of CMP with type II collagen.

There was no apparent co-localization of CMP and aggrecan in cultures of normal chondrocytes. However, material remaining after treatment with testicular hyaluronidase reacted with antibodies to the aggrecan core protein and co-localized with the filamentous CMP/type II collagen pattern.

To examine the ultrastructural associations of CMP with the cartilage extracellular matrix, chondrocytes in culture were examined after immunoperoxidase reactions. A periodic distribution of CMP along the network of collagen fibrils was observed at both low and high magnification. The ultrastructural immunostaining pattern for type II collagen was similarly periodic. Quantitative analysis revealed a periodic repeat of 59.3 nm (standard error=±0.6 nm) for CMP and 60.3 nm (standard error=±0.6 nm) for type II collagen. This observed repeat is consistent with the 60–65 nm periodicity known to be characteristic of type II collagen. The normal serum control appeared non-reactive.

Cell Culture

Chondrocytes were obtained from the sterna of 15 day-old White Leghorn chicken embryos as described by Cahn et al., *Methods in Development Biology*, Wilt et al. (Eds.), Thomas Y. Crowell Co., New York pp. 493–530 (1967). For immunofluorescence studies, cells were cultured in monolayer on gelatinized, carbon coated-coverslips at a density of $6 \times 10^5$ cells per 60 mm tissue culture dish in 3 ml Ham's F-12 medium containing 10% fetal bovine serum and 1% antibiotic-antimycotic mix. Cultures were fed fresh medium containing 50 mM ascorbic acid on days 3 and 4 and fed again 2 hr before fixation in 75% ethanol. For immunoelectron microscopy, cells were cultured on gelatinized 35 mm tissue culture dishes at equivalent densities in 1.5 ml of the same medium. Cell cultures were fed fresh medium with ascorbate as described above prior to fixation with 2.5% glutaraldehyde on day 5.

Immunofluorescent Staining

At 5 days of culture, chondrocytes were washed several times with Hank's Balanced Salt Solution (HESS), fixed with 75% ethanol and prepared for immunofluorescence staining as described in Vertel et al., *J. Cell. Biochem.* 27:215 (1985). In some experiments, glycosaminoglycans were removed from extracellular aggrecan prior to fixation by a brief digestion with testicular hyaluronidase (Vertel et al., 1985).

Cells were incubated for 20 min. at room temperature with primary antibodies and FITC or TRITC-coupled secondary antibodies as indicated in the figure legends. Cells were washed extensively with HBSS between antibody incubations. After further washes with HBSS, the coverslips were mounted in phosphate buffer/glycerol (1:9, v/v). Samples were observed and photographed using a Leitz Ortholux microscope with phase and epifluorescence optics. Fields were selected from double-stained specimens and photographed sequentially for FITC and TRITC staining.

Immunoelectron Microscopy

After 5 days of culture as described above, chondrocytes were fixed in 2.5% glutaraldehyde for 30 min. Immunoperoxidase studies with mouse monoclonal III-D5 anti-CMP and rabbit anti-type II collagen were conducted according to the procedure of Brown et al., (*Cell* 36:295, 1984), with some modifications (Vertel et al., *J. Cell. Biol.* 108:1327, 1989). Samples were counterstained for 5 min with Reynolds lead citrate and observed and photographed using a Zeiss 10 electron microscope.

Analysis of the periodicity of CMP and type II collagen immunostaining was performed using a computer assisted image analysis system and Microcomp software. Actual readings were taken directly from photographic prints of electron micrograph negatives magnified 4.65x. Seven samples were measured from each enlargement. Measurements of over 200 samples were used in each group. Absolute calibrations were based on the use of a carbon replica standard. All electron micrographs and enlargements were photographed, developed, and printed at the same magnifications during the same photographic sessions.

Electrophoresis

SDS-PAGE (Laemmli, 1970) was carried out on gels of various acrylamide concentrations, as indicated in the figure legends, blotted (Towbin et al., 1979) to Immobilon-P (Millipore Corp., Bedford, Mass.), and stained using the above antibodies followed by alkaline phosphatase conjugated goat anti-mouse IgG (H+L) or goat anti-rabbit IgG (H+L) (Biorad Laboratories) as appropriate, and using 6-bromo-4-chloro-3-indolyphosphate p-toluidine salt/nitroblue tetrazolium chloride (Gibco BRL, Gaithersburg, Md.) as chromogenic substrate.

CMP Influences Fibrillogenesis

A fibrillogenesis assay (performed as described below) demonstrated that CMP affects fibrillogenesis. Referring to FIG. 1, which depicts the results of an assay in which fibrillogenesis is monitored by measuring turbidity of a type II collagen solution in the presence and absence of CMP, CMP substantially increased turbidity. Similar results were observed using type I collagen. In both instances microscopic examination revealed that fibrils formed in the presence of CMP were thinner than those formed in the absence of CMP.

Fibrillogenesis Assay

The assay was performed essentially as described by Hedbom et al. (*J. Biol. Chem.* 264:6898, 1989). Briefly, fibrillogenesis was initiated by the addition of type II collagen to fibrillogenesis buffer (60 mM NaCl, 30 mM NaPO$_4$ [pH 7.3]) in the presence or absence of CMP. The final type II collagen concentration was 200 µg/ml, the final CMP concentration was 20 µg/ml. Fibrillogenesis was monitored by periodically measuring the optical density of the mixture at 400 nM over the course of several hours. The reaction was carried out at 37° C.

CMP-1 and CMP-2 Mediate Type II Collagen Binding

CMP-1 (amino acids 30 to 220 of CMP) and CMP-2 (amino acids 262–450 of CMP) are important for collagen binding. An in vitro assay, performed as described above, demonstrated that both CMP-1 and CMP-2 can bind type II collagen. In these experiments various portions of CMP coding sequence were used to generate *E. coli* maltose binding protein (MBP)/CMP fusion proteins (New England Biolabs, Beverly, Mass.). The fusion proteins were expressed in *E. coli*, and purified using an amylose-sepharose column. Eluate was applied to plates of immobilized type II collagen. Fusion proteins were then detected using either anti-maltose binding protein or anti-CMP monoclonal antibodies in combination with an alkaline phosphatase conjugated secondary antibody.

Figure 2:
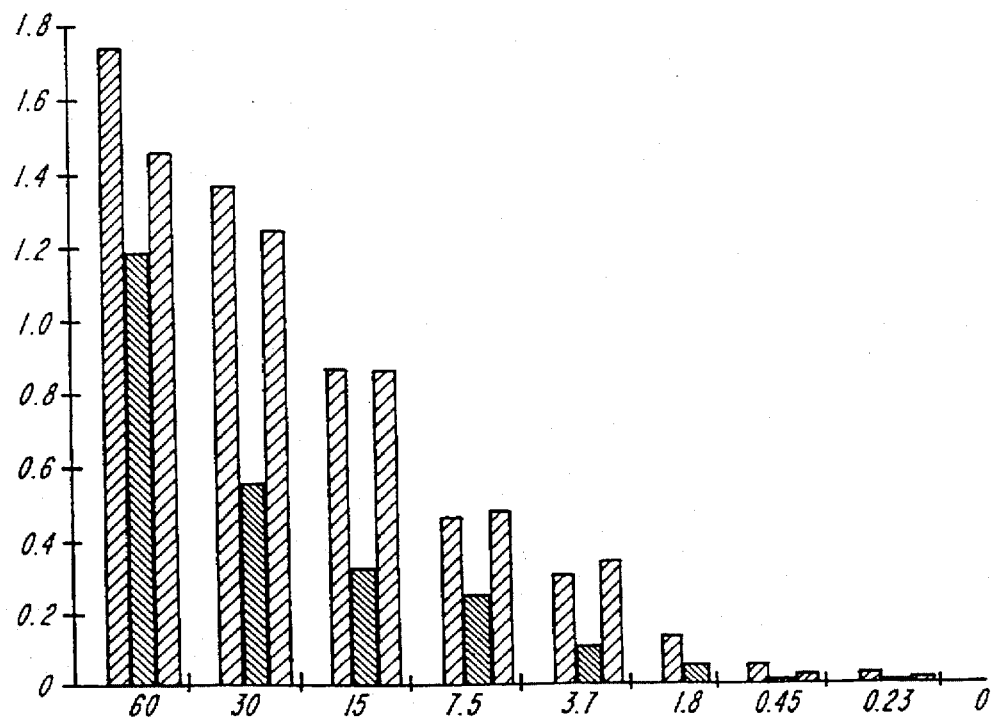
FIG. 2 is a graph which depicts the results of a collagen binding assay. Relative binding is plotted as a function of CMP concentration (μg/ml).

FIG. 2 illustrates the results of assays of three different fusion proteins. The relative amount of binding is shown as a function of the concentration of fusion protein (in µg/ml) for MBP fused to amino acids 1–450 of chicken CMP (first bar in each group); MBP fused to chicken CMP-1 (second bar in each group); and MBP fused to amino chicken CMP-2 (third bar in each group). Binding was detected with anti-MBP antiserum.

Collagen Binding Assay

Plates were coated with a 1:75 dilution in PBS-T of 2 mg/ml type II collagen (Nitta Gelatin Inc., Osaka, Japan) and then dried for ca. 18 hr at 37° C. Fusions proteins, purified as described above, were applied to the collagen coated plates and incubated for 1 hr at 37° C. Fusion proteins were detected with anti-MBP antiserum (New England Biolabs, Beverly, Mass.) or anti-CMP antibody (described above) and a secondary antibody essentially as described above.

Collagen-Binding Fragments of CMP-1 and CMP-2

Construction of MBP-CMP-1 and MBP-CMP-2 Fusion Proteins.

The CMP-1 domain was synthesized by PCR using a 5' primer sequence corresponding to amino acid residue 24 (first amino acid of the mature protein) to amino acid residue 30 and a 3' primer sequence corresponding to amino acid residues 214 through 220. The CMP-2 fragment was amplified by using a 5' primer sequence corresponding to amino acid residues 262–268, and a 3' primer sequence corresponding to amino acid residues 444–450. The PCR fragments were cloned by blunt end ligation into the StuI cloning site of the maltose binding protein encoding vector pMAL-C2 (New England Biolabs, Beverly, Mass.). Miniprep DNA samples were digested with the restriction enzyme BamHI (BamHI sites are located in the MBP polylinker at the 5' and 3' ends of the inserted CMP fragment) and the appropriate clones were screened for the presence of insert fragments of the expected size. Positive clones were next screened for expression of fusion protein by Western blotting of SDS-PAGE separated proteins and testing for cross reactivity with anti-CMP antibodies and alkaline phosphatase linked secondary antibodies.

Expression and purification of MBP-CMP-1 and MBP-CMP-2 Fusion Proteins

The expression of CMP-1 or CMP-2 fusion proteins in MBP vectors was induced by addition of IPTG to cultures of logarithmically growing E. coli cultures as described in the New England Biolabs pMAL protocol. The expressed protein was purified on amylose resin as described in the New England Biolabs protocol. Briefly, the cells were pelleted by centrifugation (5000 RPM, in Sorvoll SS 34 rotor, 10 Min. at 4° C.), washed in column buffer (20 mM Tris-Cl pH 7.4, 200 mM NaCl, mM EDTA, 1 mM EGTA, 1 mM DTT, 1 mM sodium azide), lysed in the same buffer by resuspending cells in 1/100th of the original culture volume and sonication. The cell debris was pelleted by centrifugation at 20,000 g for 30 minutes. The supernate was applied to an amylose column using 50 ml of resin for each one liter of bacterial culture. The column was washed with 10 column volumes of column buffer, and the bound fusion protein was eluted with the column buffer supplemented with 10 mM maltose.

Construction of Deletions of MBP-CMP1 and MBP-CMP2

Deletions of MBP-CMP1 and MBP-CMP2 were made in order to allow more precise delineation of the collagen binding sites of CMP. The MBP-CMP2 (or MBP-CMP1) plasmid was linearized at its unique XbaI site (this site is located in the polylinker sequence of pMLA-c at the 3' of the CMP2 (or CMP1) fragment). The linearized plasmid was digested with Bal31 exonuclease (at an enzyme concentration that theoretically would digest DNA at the rate 100 base pairs per minute per end) and aliquots of the reaction mixture removed at one minute intervals. The Bal31 digestion was stopped by addition of EGTA. Phenol and phenol/chloroform extractions were performed and the DNA ethanol precipitated. The ends of the DNA were repaired by Klenow, and ligated with 50 molar excess of the Pharmacia Suppressible Termination Linker (Pharmacia, Piscataway, N.J.). The sequence of this oligonucleotide contains a translation stop codon in each of the three reading frames as well as introducing a unique XbaI restriction site into the clones. E. coli XL1 Blue cells (Stratagene, San Diego, Calif.) were transformed with the ligated DNA by electroporation. The colonies were screened for presence of shortened MBP-CMP2 plasmids by digestion of miniprep DNA with XbaI. Putative clones containing shortened plasmids were induced by IPTG and screened for expression of fusion proteins by SDS-PAGE. Fusion proteins were purified from selected colonies and screened (by ELISA) for the ability to bind to type II collagen.

Detection of Collagen Binding by CMP Fragments

The measurement of the binding of the CMP constructs to collagen were performed using the ELISA methods described above.

Determination of the Molecular Weights of MBP-CMP and MBP-CMP and Deletion Fusion Proteins The molecular weight of the purified MBP-CMP-1 and MBP-CMP-2 fusion proteins and their Bal31-generated truncated versions were estimated from the distance migrated by the proteins after electrophoresis on 10% polyacrylamide gels. Protein standards with known molecular weights were electrophoresed in separate lanes of the same gel. The molecular weights of the standard were plotted as a function of their distance migrated. The molecular weights of the MBP fusion proteins were estimated from the distance migrated on these gels.

Determination of molecular weight of and the number of amino acids in the CMP regions of the MBP-CMP fusion proteins Since the fusion proteins include both the MBP (43,000 daltons) and a CMP domain (or fragment thereof), the molecular weight of the CMP component of a fusion protein was determined by subtracting the molecular weight of the MBP from that of the fusion protein. This net molecular weight (i.e. that of the CMP component) was divided by the average molecular weight of an amino acid (110) to obtain an estimate of the number of amino acids of the CMP domains.

Identification of a region in CMP-1 and CMP-2 which is responsible for binding to collagen Fusion genes encoding MBP-CMP-1 and MBP-CMP-2 were subjected to Bal31 digestion to generate terminal deletions in the CMP-domain-encoding region of the fusion gene. Fusion proteins, with truncated CMP domains, were tested for the ability to bind collagen. As is shown in Table I, deletion of up to 145 residues from the C-terminal end of the CMP domain of the fusion protein did not prevent binding to collagen. Thus, approximately 45 amino acid residues at the N-terminal end of CMP-1 and CMP-2 is or contains a region critical to collagen binding. This approximately 45 amino acid residue region corresponds approximately to amino acid residues 24–68 of CMP-1 (A P P Q P R G T L C R T K P T D L V F I I D S S R S V R P Q E F E K V K V F L S R V I E G (SEQ. ID. NO: 38)) and to amino acid residues 262–306 of CMP-2 (A C S G G S G S A L D L V F L I D G S K S V R P E N F E L V K K F I N Q I V E S L E V S E (SEQ. ID. NO: 39)) in the chicken protein (by the numbering system of Kiss et al.) and to amino acid residues 27–71 of CMP-1 (A P Q S R G H L C R T R P T D L V F V V D S S R S V R P V E F E K V K V F L S Q V I E S L D (SEQ. ID. NO: 40)) and to amino acid residues 264–309 of CMP-2 (V C S G G G G S S A T D L V F L I D G S K S V R P E N X E L V K K F I S Q I V D T L D V S D (SEQ. ID. NO: 41)) in the human protein (by the numbering system of Jenkins et al.).

The collagen binding sequence 1 (CBS1) motif

Within the 45 amino acid region is a smaller region of approximately 8 to 10 residues in length, referred to as The collagen binding sequence 1 (CBS1) motif, which is common to many proteins which bind collagen. Its sequence, in the chicken CMP-1 gene is T-D-L-V-F-I-I-D-S-S (SEQ. ID. NO: 42). Its sequence, in the chicken CMP-2 gene is L-D-L-V-F-L-I-D-G-S (SEQ. ID. NO: 43). The sequence is located at approximately amino acid residues 38–47 of CMP-1 and amino acid residues 271–280 of CMP-2 in the chicken protein (by the numbering system of Kiss et al.) and at approximately amino acid residues 40–49 of CMP-1 and amino acid residues 274–283 of CMP-2 in the human protein (by the numbering system of Jenkins et al.).

TABLE I

| Fusion Protein Clone Number | Estimated Molecular Wt. Of Fusion Protein | Molecular Wt of CMP Fragment [Est. m.w. of fusion protein-m.w. of MBP (43,000)] | Estimated Number of Amino Acids in CMP Fragment | Collagen Binding |
|---|---|---|---|---|
| MBP-CMP1 | 67,000 | 24,000 | 218 | YES |
| MBP-CMP1-Δ22.1 | 48,000 | 5,000 | 45 | YES |
| MBP-CMP2 | 68,000 | 25,000 | 227 | YES |
| MBP-CMP2-Δ4.1 | 58,000 | 15,000 | 136 | YES |
| MBP-CMP2-Δ40.1 | 53,000 | 10,000 | 91 | YES |
| MBP-CMP2-Δ23.2 | 48,000 | 5,000 | 45 | YES |
| MBP-CMP2-Δ46.2 | 43,000 | 0 | 0 | NO |
| MBP-CMP2-Δ47.2 | 43,000 | 0 | 0 | NO |
| MBP | 43,000 | 0 | 0 | NO |

USE

The collagen-binding CMP polypeptides of the invention may be used to deliver therapeutic, diagnostic, cosmetic or other compounds to collagenous tissue. For example an imaging agent such as a fluorescent or radioactive label can be attached to a collagen-binding CMP polypeptide and the conjugate can be used to visualize and analyze the structure of collagenous tissue. A therapeutic agent capable of influencing the structure of collagenous tissue, e.g., collagenase, may be attached to collagen-binding CMP polypeptide and thus delivered to collagenous tissue. In a similar manner an anti-cancer drug may be delivered to collagenous tissue. Compounds designed for cosmetic purposes, e.g, for increasing hydration, may be delivered to collagenous tissue, e.g., skin, by covalent attachment to a collagen-binding CMP polypeptide.

To effect delivery a compound, e.g., a protein, is generally covalently attached to a collagen-binding CMP peptide. Many techniques for covalently linking polypeptides are known to those skilled in the art. For example, succinimidyloxycarbonyl-α-methyl-α-(2-pyridyldithio)-toluene and N-succinimidyl 3-(2-pyridyldthio)propionate (Pierce, Rockford, Ill.) are heterobifunctional cross-linkers which can be used to link proteins in a step-wise fashion avoiding the formation of homopolymers and other undesirable side reactions. Alternatively genetically-engineered fusion proteins can be created to link CMP and a protein to be delivered to collagenous tissue. In addition the amino acid sequence of CMP, or polypeptide fragments thereof may be modified to permit attachment of particular compounds. For example, site-directed mutagenesis could be used to introduce an attachment site for glycosaminoglycan in CMP. The EGF-like domain could modified to introduce such an attachment site. Modification of the EGF-like domain will not be apt to interfere with binding of CMP to collagen.

Polypeptides of the invention can be applied to a surface to promote the attachment (e.g., by covalent or noncovalent association) of collagen to the surface, e.g., the surface of a tissue, e.g., the surface of a tooth or gum, or the surface of a medical device, e.g., a device to be implanted in the body.

CMP or fragments thereof which affect fibrillogenesis can be used to form collagen fibrils. Fibrils so formed can be used as a prosthetic to replace components of skin or other collagenous tissue or as a coating material that will enhance biocompatibility of prosthetic devices.

SEQUENCE LISTING ( 1 ) GENERAL INFORMATION:

( i i i ) NUMBER OF SEQUENCES: 43

( 2 ) INFORMATION FOR SEQ ID NO:1:

( i ) SEQUENCE CHARACTERISTICS:
( A ) LENGTH: 10 amino acids
( B ) TYPE: amino acid
( D ) TOPOLOGY: linear ( x i ) SEQUENCE DESCRIPTION: SEQ ID NO:1:

Thr Asp Leu Val Phe Ile Ile Asp Ser Ser
1               5                   10

( 2 ) INFORMATION FOR SEQ ID NO:2:

( i ) SEQUENCE CHARACTERISTICS:
( A ) LENGTH: 10 amino acids
( B ) TYPE: amino acid
( D ) TOPOLOGY: linear ( x i ) SEQUENCE DESCRIPTION: SEQ ID NO:2:

Leu Asp Leu Val Phe Leu Ile Asp Gly Ser
1               5                   10

( 2 ) INFORMATION FOR SEQ ID NO:3:

( i ) SEQUENCE CHARACTERISTICS:
( A ) LENGTH: 10 amino acids
( B ) TYPE: amino acid
( D ) TOPOLOGY: linear ( x i ) SEQUENCE DESCRIPTION: SEQ ID NO:3:

Thr Asp Leu Val Phe Val Val Asp Ser Ser
1               5                   10

( 2 ) INFORMATION FOR SEQ ID NO:4:

( i ) SEQUENCE CHARACTERISTICS:
( A ) LENGTH: 10 amino acids
( B ) TYPE: amino acid
( D ) TOPOLOGY: linear ( x i ) SEQUENCE DESCRIPTION: SEQ ID NO:4:

Thr Asp Leu Val Phe Leu Ile Asp Gly Ser
1               5                   10

( 2 ) INFORMATION FOR SEQ ID NO:5:

( i ) SEQUENCE CHARACTERISTICS:
( A ) LENGTH: 9 amino acids
( B ) TYPE: amino acid
( D ) TOPOLOGY: linear ( x i ) SEQUENCE DESCRIPTION: SEQ ID NO:5:

Asp Ile Val Phe Leu Thr Asp Ala Ser
1               5

( 2 ) INFORMATION FOR SEQ ID NO:6:

( i ) SEQUENCE CHARACTERISTICS:
( A ) LENGTH: 9 amino acids
( B ) TYPE: amino acid
( D ) TOPOLOGY: linear ( x i ) SEQUENCE DESCRIPTION: SEQ ID NO:6:

Asp Ile Val Leu Leu Val Asp Gly Ser
1               5

( 2 ) INFORMATION FOR SEQ ID NO:7:

( i ) SEQUENCE CHARACTERISTICS:
( A ) LENGTH: 9 amino acids
( B ) TYPE: amino acid
( D ) TOPOLOGY: linear ( x i ) SEQUENCE DESCRIPTION: SEQ ID NO:7:

Asp Leu Val Phe Leu Val Asp Gly Ser
1               5

( 2 ) INFORMATION FOR SEQ ID NO:8:

( i ) SEQUENCE CHARACTERISTICS:
( A ) LENGTH: 9 amino acids
( B ) TYPE: amino acid
( D ) TOPOLOGY: linear ( x i ) SEQUENCE DESCRIPTION: SEQ ID NO:8:

Asp Val Val Phe Leu Val Asp Gly Ser
1               5

( 2 ) INFORMATION FOR SEQ ID NO:9:

( i ) SEQUENCE CHARACTERISTICS:
    ( A ) LENGTH: 9 amino acids
    ( B ) TYPE: amino acid
    ( D ) TOPOLOGY: linear ( x i ) SEQUENCE DESCRIPTION: SEQ ID NO:9:

Asp Leu Val Phe Leu Val Asp Gly Ser
1               5

( 2 ) INFORMATION FOR SEQ ID NO:10:

( i ) SEQUENCE CHARACTERISTICS:
    ( A ) LENGTH: 9 amino acids
    ( B ) TYPE: amino acid
    ( D ) TOPOLOGY: linear ( x i ) SEQUENCE DESCRIPTION: SEQ ID NO:10:

Asp Leu Val Phe Ile Ile Asp Ser Ser
1               5

( 2 ) INFORMATION FOR SEQ ID NO:11:

( i ) SEQUENCE CHARACTERISTICS:
    ( A ) LENGTH: 9 amino acids
    ( B ) TYPE: amino acid
    ( D ) TOPOLOGY: linear ( x i ) SEQUENCE DESCRIPTION: SEQ ID NO:11:

Asp Leu Val Phe Leu Ile Asp Gly Ser
1               5

( 2 ) INFORMATION FOR SEQ ID NO:12:

( i ) SEQUENCE CHARACTERISTICS:
    ( A ) LENGTH: 9 amino acids
    ( B ) TYPE: amino acid
    ( D ) TOPOLOGY: linear ( x i ) SEQUENCE DESCRIPTION: SEQ ID NO:12:

Asp Ile Met Leu Leu Val Asp Ser Ser
1               5

( 2 ) INFORMATION FOR SEQ ID NO:13:

( i ) SEQUENCE CHARACTERISTICS:
    ( A ) LENGTH: 9 amino acids
    ( B ) TYPE: amino acid
    ( D ) TOPOLOGY: linear ( x i ) SEQUENCE DESCRIPTION: SEQ ID NO:13:

Asp Leu Leu Phe Val Leu Asp Ser Ser
1               5

( 2 ) INFORMATION FOR SEQ ID NO:14:

( i ) SEQUENCE CHARACTERISTICS:
    ( A ) LENGTH: 9 amino acids
    ( B ) TYPE: amino acid
    ( D ) TOPOLOGY: linear ( x i ) SEQUENCE DESCRIPTION: SEQ ID NO:14:

Asp Leu Phe Phe Val Leu Asp Thr Ser (2) INFORMATION FOR SEQ ID NO:15:

(i) SEQUENCE CHARACTERISTICS:
       (A) LENGTH: 9 amino acids
       (B) TYPE: amino acid
       (D) TOPOLOGY: linear (xi) SEQUENCE DESCRIPTION: SEQ ID NO:15:

Asp Ile Val Phe Leu Leu Asp Gly Ser
   1               5

(2) INFORMATION FOR SEQ ID NO:16:

(i) SEQUENCE CHARACTERISTICS:
       (A) LENGTH: 9 amino acids
       (B) TYPE: amino acid
       (D) TOPOLOGY: linear (xi) SEQUENCE DESCRIPTION: SEQ ID NO:16:

Asp Ile Met Phe Val Ile Asp Ser Ser
   1               5

(2) INFORMATION FOR SEQ ID NO:17:

(i) SEQUENCE CHARACTERISTICS:
       (A) LENGTH: 9 amino acids
       (B) TYPE: amino acid
       (D) TOPOLOGY: linear (xi) SEQUENCE DESCRIPTION: SEQ ID NO:17:

Asp Ile Ala Phe Ile Met Asp Ser Ser
   1               5

(2) INFORMATION FOR SEQ ID NO:18:

(i) SEQUENCE CHARACTERISTICS:
       (A) LENGTH: 9 amino acids
       (B) TYPE: amino acid
       (D) TOPOLOGY: linear (xi) SEQUENCE DESCRIPTION: SEQ ID NO:18:

Glu Leu Ala Phe Ala Ile Asp Thr Ser
   1               5

(2) INFORMATION FOR SEQ ID NO:19:

(i) SEQUENCE CHARACTERISTICS:
       (A) LENGTH: 9 amino acids
       (B) TYPE: amino acid
       (D) TOPOLOGY: linear (xi) SEQUENCE DESCRIPTION: SEQ ID NO:19:

Asp Val Ile Leu Gly Phe Asp Val Ser
   1               5

(2) INFORMATION FOR SEQ ID NO:20:

(i) SEQUENCE CHARACTERISTICS:
       (A) LENGTH: 9 amino acids
       (B) TYPE: amino acid
       (D) TOPOLOGY: linear (xi) SEQUENCE DESCRIPTION: SEQ ID NO:20:

Asp Ile Val Phe Leu Leu Asp Gly Ser
   1               5

( 2 ) INFORMATION FOR SEQ ID NO:21:

( i ) SEQUENCE CHARACTERISTICS:
        ( A ) LENGTH: 9 amino acids
        ( B ) TYPE: amino acid
        ( D ) TOPOLOGY: linear ( x i ) SEQUENCE DESCRIPTION: SEQ ID NO:21:

Asp  Val  Val  Phe  Leu  Ile  Asp  Ser  Ser
  1                          5

( 2 ) INFORMATION FOR SEQ ID NO:22:

( i ) SEQUENCE CHARACTERISTICS:
        ( A ) LENGTH: 9 amino acids
        ( B ) TYPE: amino acid
        ( D ) TOPOLOGY: linear ( x i ) SEQUENCE DESCRIPTION: SEQ ID NO:22:

Asp  Val  Val  Phe  Leu  Val  Asp  Gly  Ser
  1                          5

( 2 ) INFORMATION FOR SEQ ID NO:23:

( i ) SEQUENCE CHARACTERISTICS:
        ( A ) LENGTH: 9 amino acids
        ( B ) TYPE: amino acid
        ( D ) TOPOLOGY: linear ( x i ) SEQUENCE DESCRIPTION: SEQ ID NO:23:

Asp  Val  Val  Phe  Leu  Ile  Asp  Gly  Ser
  1                          5

( 2 ) INFORMATION FOR SEQ ID NO:24:

( i ) SEQUENCE CHARACTERISTICS:
        ( A ) LENGTH: 9 amino acids
        ( B ) TYPE: amino acid
        ( D ) TOPOLOGY: linear ( x i ) SEQUENCE DESCRIPTION: SEQ ID NO:24:

Asp  Ile  Leu  Phe  Leu  Ile  Asp  Gly  Ser
  1                          5

( 2 ) INFORMATION FOR SEQ ID NO:25:

( i ) SEQUENCE CHARACTERISTICS:
        ( A ) LENGTH: 9 amino acids
        ( B ) TYPE: amino acid
        ( D ) TOPOLOGY: linear ( x i ) SEQUENCE DESCRIPTION: SEQ ID NO:25:

Asp  Ile  Ile  Phe  Leu  Leu  Asp  Gly  Ser
  1                          5

( 2 ) INFORMATION FOR SEQ ID NO:26:

( i ) SEQUENCE CHARACTERISTICS:
        ( A ) LENGTH: 9 amino acids
        ( B ) TYPE: amino acid
        ( D ) TOPOLOGY: linear ( x i ) SEQUENCE DESCRIPTION: SEQ ID NO:26:

Asp  Ile  Val  Phe  Leu  Ile  Asp  Gly  Ser
  1                          5

( 2 ) INFORMATION FOR SEQ ID NO:27:

(i) SEQUENCE CHARACTERISTICS:
   (A) LENGTH: 9 amino acids
   (B) TYPE: amino acid
   (D) TOPOLOGY: linear (xi) SEQUENCE DESCRIPTION: SEQ ID NO:27:

Asp Leu Ile Phe Leu Ile Asp Gly Ser
1               5

(2) INFORMATION FOR SEQ ID NO:28:

(i) SEQUENCE CHARACTERISTICS:
      (A) LENGTH: 9 amino acids
      (B) TYPE: amino acid
      (D) TOPOLOGY: linear (xi) SEQUENCE DESCRIPTION: SEQ ID NO:28:

Asp Leu Val Phe Leu Leu Asp Gly Ser
1               5

(2) INFORMATION FOR SEQ ID NO:29:

(i) SEQUENCE CHARACTERISTICS:
      (A) LENGTH: 9 amino acids
      (B) TYPE: amino acid
      (D) TOPOLOGY: linear (xi) SEQUENCE DESCRIPTION: SEQ ID NO:29:

Asp Val Ala Phe Val Leu Glu Gly Ser
1               5

(2) INFORMATION FOR SEQ ID NO:30:

(i) SEQUENCE CHARACTERISTICS:
      (A) LENGTH: 9 amino acids
      (B) TYPE: amino acid
      (D) TOPOLOGY: linear (xi) SEQUENCE DESCRIPTION: SEQ ID NO:30:

Asp Val Ile Leu Leu Leu Asp Gly Ser
1               5

(2) INFORMATION FOR SEQ ID NO:31:

(i) SEQUENCE CHARACTERISTICS:
      (A) LENGTH: 9 amino acids
      (B) TYPE: amino acid
      (D) TOPOLOGY: linear (xi) SEQUENCE DESCRIPTION: SEQ ID NO:31:

Asp Ile Val Phe Leu Ile Asp Gly Ser
1               5

(2) INFORMATION FOR SEQ ID NO:32:

(i) SEQUENCE CHARACTERISTICS:
      (A) LENGTH: 9 amino acids
      (B) TYPE: amino acid
      (D) TOPOLOGY: linear (xi) SEQUENCE DESCRIPTION: SEQ ID NO:32:

Asp Ile Val Phe Leu Ile Asp Gly Ser
1               5

(2) INFORMATION FOR SEQ ID NO:33:

(i) SEQUENCE CHARACTERISTICS:

(A) LENGTH: 9 amino acids
(B) TYPE: amino acid
(D) TOPOLOGY: linear (xi) SEQUENCE DESCRIPTION: SEQ ID NO:33:

Asp Leu Val Phe Leu Phe Asp Gly Ser
1               5

(2) INFORMATION FOR SEQ ID NO:34:

(i) SEQUENCE CHARACTERISTICS:
    (A) LENGTH: 9 amino acids
    (B) TYPE: amino acid
    (D) TOPOLOGY: linear (xi) SEQUENCE DESCRIPTION: SEQ ID NO:34:

Asp Ile Val Ile Val Leu Asp Gly Ser
1               5

(2) INFORMATION FOR SEQ ID NO:35:

(i) SEQUENCE CHARACTERISTICS:
    (A) LENGTH: 9 amino acids
    (B) TYPE: amino acid
    (D) TOPOLOGY: linear (xi) SEQUENCE DESCRIPTION: SEQ ID NO:35:

Asp Val Val Leu Val Cys Asp Glu Ser
1               5

(2) INFORMATION FOR SEQ ID NO:36:

(i) SEQUENCE CHARACTERISTICS:
    (A) LENGTH: 9 amino acids
    (B) TYPE: amino acid
    (D) TOPOLOGY: linear (xi) SEQUENCE DESCRIPTION: SEQ ID NO:36:

Asp Ile Ser Phe Leu Leu Asp Val Ser
1               5

(2) INFORMATION FOR SEQ ID NO:37:

(i) SEQUENCE CHARACTERISTICS:
    (A) LENGTH: 496 amino acids
    (B) TYPE: amino acid
    (D) TOPOLOGY: linear (xi) SEQUENCE DESCRIPTION: SEQ ID NO:37:

Met Arg Val Leu Ser Gly Thr Ser Leu Met Leu Cys Ser Leu Leu Leu
1               5                   10                  15

Leu Leu Gln Ala Leu Cys Ser Pro Gly Leu Ala Pro Gln Ser Arg Gly
                20                  25                  30

His Leu Cys Arg Thr Arg Pro Thr Asp Leu Val Phe Val Val Asp Ser
            35                  40                  45

Ser Arg Ser Val Arg Pro Val Glu Phe Glu Lys Val Lys Val Phe Leu
        50                  55                  60

Ser Gln Val Ile Glu Ser Leu Asp Val Gly Pro Asn Ala Thr Arg Val
65                  70                  75                  80

Gly Met Val Asn Tyr Ala Ser Thr Val Lys Gln Glu Phe Ser Leu Arg
                85                  90                  95

Ala His Val Ser Lys Ala Ala Leu Leu Gln Ala Val Arg Arg Ile Gln
                100                 105                 110

Pro Leu Ser Thr Gly Thr Met Thr Gly Leu Ala Ile Gln Phe Ala Ile

|     |     |     |     |     | 115 |     |     |     |     | 120 |     |     |     |     | 125 |     |     |
|-----|-----|-----|-----|-----|-----|-----|-----|-----|-----|-----|-----|-----|-----|-----|-----|-----|-----|

Thr Lys Ala Phe Gly Asp Ala Glu Gly Gly Arg Ser Arg Ser Pro Asp
    130                 135                 140

Ile Ser Lys Val Val Ile Val Val Thr Asp Gly Arg Pro Gln Asp Ser
145                 150                 155                 160

Val Gln Asp Val Ser Ala Arg Ala Arg Ala Ser Gly Val Glu Leu Phe
                165                 170                 175

Ala Ile Gly Val Gly Ser Val Asp Lys Ala Thr Leu Arg Gln Ile Ala
            180                 185                 190

Ser Glu Pro Gln Asp Glu His Val Asp Tyr Val Glu Ser Tyr Ser Val
        195                 200                 205

Ile Glu Lys Leu Ser Arg Lys Phe Gln Glu Ala Phe Cys Val Val Ser
    210                 215                 220

Asp Leu Cys Ala Thr Gly Asp His Asp Cys Glu Gln Val Cys Ile Ser
225                 230                 235                 240

Ser Pro Gly Ser Tyr Thr Cys Ala Cys His Glu Gly Phe Thr Leu Asn
                245                 250                 255

Ser Asp Gly Lys Thr Cys Asn Val Cys Ser Gly Gly Gly Ser Ser
            260                 265                 270

Ala Thr Asp Leu Val Phe Leu Ile Asp Gly Ser Lys Ser Val Arg Pro
        275                 280                 285

Glu Asn Phe Glu Leu Val Lys Lys Phe Ile Ser Gln Ile Val Asp Thr
    290                 295                 300

Leu Asp Val Ser Asp Lys Leu Ala Gln Val Gly Leu Val Gln Tyr Ser
305                 310                 315                 320

Ser Ser Val Arg Gln Glu Phe Pro Leu Gly Arg Phe His Thr Lys Lys
                325                 330                 335

Asp Ile Lys Ala Ala Val Arg Asn Met Ser Tyr Met Glu Lys Gly Thr
            340                 345                 350

Met Thr Gly Ala Ala Leu Lys Tyr Leu Ile Asp Asn Ser Phe Thr Val
        355                 360                 365

Ser Ser Gly Ala Arg Pro Gly Ala Gln Lys Val Gly Ile Val Phe Thr
    370                 375                 380

Asp Gly Arg Ser Gln Asp Tyr Ile Asn Asp Ala Ala Lys Lys Ala Lys
385                 390                 395                 400

Asp Leu Gly Phe Lys Met Phe Ala Val Gly Val Gly Asn Ala Val Glu
                405                 410                 415

Asp Glu Leu Arg Glu Ile Ala Ser Glu Pro Val Ala Glu His Tyr Phe
            420                 425                 430

Tyr Thr Ala Asp Phe Lys Thr Ile Asn Gln Ile Gly Lys Lys Leu Gln
        435                 440                 445

Lys Lys Ile Cys Val Glu Glu Asp Pro Cys Ala Cys Glu Ser Leu Val
    450                 455                 460

Lys Phe Gln Ala Lys Val Glu Gly Leu Leu Gln Ala Leu Thr Arg Lys
465                 470                 475                 480

Leu Glu Ala Val Ser Lys Arg Leu Ala Ile Leu Glu Asn Thr Val Val
                485                 490                 495

(2) INFORMATION FOR SEQ ID NO:38:

(i) SEQUENCE CHARACTERISTICS:
 (A) LENGTH: 45 amino acids
 (B) TYPE: amino acid
 (D) TOPOLOGY: linear (xi) SEQUENCE DESCRIPTION: SEQ ID NO:38:

```
Ala  Pro  Pro  Gln  Pro  Arg  Gly  Thr  Leu  Cys  Arg  Thr  Lys  Pro  Thr  Asp
 1              5                        10                       15

Leu  Val  Phe  Ile  Ile  Asp  Ser  Ser  Arg  Ser  Val  Arg  Pro  Gln  Glu  Phe
               20                        25                      30

Glu  Lys  Val  Lys  Val  Phe  Leu  Ser  Arg  Val  Ile  Glu  Gly
          35                        40                       45
```

( 2 ) INFORMATION FOR SEQ ID NO:39:

( i ) SEQUENCE CHARACTERISTICS:
        ( A ) LENGTH: 45 amino acids
        ( B ) TYPE: amino acid
        ( D ) TOPOLOGY: linear ( x i ) SEQUENCE DESCRIPTION: SEQ ID NO:39:

```
Ala  Cys  Ser  Gly  Gly  Ser  Gly  Ser  Ala  Leu  Asp  Leu  Val  Phe  Leu  Ile
 1              5                        10                       15

Asp  Gly  Ser  Lys  Ser  Val  Arg  Pro  Glu  Asn  Phe  Glu  Leu  Val  Lys  Lys
               20                        25                      30

Phe  Ile  Asn  Gln  Ile  Val  Glu  Ser  Leu  Glu  Val  Ser  Glu
          35                        40                       45
```

( 2 ) INFORMATION FOR SEQ ID NO:40:

( i ) SEQUENCE CHARACTERISTICS:
        ( A ) LENGTH: 46 amino acids
        ( B ) TYPE: amino acid
        ( D ) TOPOLOGY: linear ( x i ) SEQUENCE DESCRIPTION: SEQ ID NO:40:

```
Ala  Pro  Gln  Ser  Arg  Gly  His  Leu  Cys  Arg  Thr  Arg  Pro  Thr  Asp  Leu
 1              5                        10                       15

Val  Phe  Val  Val  Asp  Ser  Ser  Arg  Ser  Val  Arg  Pro  Val  Glu  Phe  Glu
               20                        25                      30

Lys  Val  Lys  Val  Phe  Leu  Ser  Gln  Val  Ile  Glu  Ser  Leu  Asp
          35                        40                       45
```

( 2 ) INFORMATION FOR SEQ ID NO:41:

( i ) SEQUENCE CHARACTERISTICS:
        ( A ) LENGTH: 46 amino acids
        ( B ) TYPE: amino acid
        ( D ) TOPOLOGY: linear ( x i ) SEQUENCE DESCRIPTION: SEQ ID NO:41:

```
Val  Cys  Ser  Gly  Gly  Gly  Gly  Ser  Ser  Ala  Thr  Asp  Leu  Val  Phe  Leu
 1              5                        10                       15

Ile  Asp  Gly  Ser  Lys  Ser  Val  Arg  Pro  Glu  Asn  Xaa  Glu  Leu  Val  Lys
               20                        25                      30

Lys  Phe  Ile  Ser  Gln  Ile  Val  Asp  Thr  Leu  Asp  Val  Ser  Asp
          35                        40                       45
```

( 2 ) INFORMATION FOR SEQ ID NO:42:

( i ) SEQUENCE CHARACTERISTICS:
        ( A ) LENGTH: 10 amino acids
        ( B ) TYPE: amino acid
        ( D ) TOPOLOGY: linear ( x i ) SEQUENCE DESCRIPTION: SEQ ID NO:42:

```
Thr  Asp  Leu  Val  Phe  Ile  Ile  Asp  Ser  Ser
 1              5                        10
```

(2) INFORMATION FOR SEQ ID NO:43:

(i) SEQUENCE CHARACTERISTICS:
        (A) LENGTH: 10 amino acids
        (B) TYPE: amino acid
        (D) TOPOLOGY: linear (xi) SEQUENCE DESCRIPTION: SEQ ID NO:43:

```
Leu Asp Leu Val Phe Leu Ile Asp Gly Ser
 1               5                   10
```

Other embodiments are within the following claims.

What is claimed is:

1. A chimeric polypeptide which includes a fragment of cartilage matrix protein domain CMP-1 or CMP-2, said fragment including a collagen binding site and said fragment being at least 99% homologous with the corresponding residues of cartilage matrix protein domain CMP-1 or CMP2.

2. The chimeric polypeptide of claim 1, wherein said fragment is 100% homologous with the corresponding residues of cartilage matrix protein domain CMP-1 or CMP2.

3. The chimeric polypeptide of claim 1, wherein said fragment is 100% homologous with the corresponding residues of cartilage matrix protein domain CMP-1 or CMP2.

4. A molecular conjugate comprising the chimeric polypeptide of claim 1 and an imaging or therapeutic agent.

* * * * *